United States Patent
Sedlmair et al.

(10) Patent No.: US 11,232,566 B2
(45) Date of Patent: Jan. 25, 2022

(54) METHOD AND SYSTEM FOR EVALUATION OF TUMOR TISSUE BY UNFOLDING MORPHOLOGICAL AND TEXTURE PROPERTIES

(71) Applicant: Siemens Healthcare GmbH, Erlangen (DE)

(72) Inventors: Martin Sedlmair, Zirndorf (DE); Bernhard Schmidt, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 9 days.

(21) Appl. No.: 16/202,256

(22) Filed: Nov. 28, 2018

(65) Prior Publication Data
US 2019/0164289 A1   May 30, 2019

(30) Foreign Application Priority Data
Nov. 30, 2017   (EP) .................... 17204732

(51) Int. Cl.
*G06T 15/08* (2011.01)
*G06T 7/00* (2017.01)
(Continued)

(52) U.S. Cl.
CPC ............ *G06T 7/0014* (2013.01); *A61B 6/032* (2013.01); *A61B 6/5217* (2013.01);
(Continued)

(58) Field of Classification Search
CPC . G06T 2207/10072; G06T 2207/30004; G06T 7/0012; G06T 2207/10081; G06T 2207/30096; G06T 7/11; G06T 7/12; G06T 7/33; G06T 2207/20104; G06T 7/174; G06T 2200/04; G06T 2207/10088; G06T 2207/10124; G06T 2207/10132; G06T 2207/20081; G06T 2207/30008; G06T 7/143; G06T 2207/30048; G06T 7/50; G06T 7/13; G06T 2207/20076;
(Continued)

(56) References Cited

U.S. PATENT DOCUMENTS 6,181,348 B1   1/2001   Geiger
6,443,894 B1   9/2002   Sumanaweera et al.
(Continued)

OTHER PUBLICATIONS

Castellano, Gabriela et al. "Texture analysis of medical images" Clinical Radiology, vol. 59, No. 12, pp. 1061-1069, Dec. 2004 // DOI: 10.1016/j.crad.2004.07.006.
(Continued)

*Primary Examiner* — Quan M Hua
(74) *Attorney, Agent, or Firm* — Harness, Dickey & Pierce, P.L.C.

(57) ABSTRACT

A method and system are for analyzing an anatomical structure of interest in 3D image data. In an embodiment, the method includes segmenting a first contour of the structure of interest in the 3D image data, the first contour defining a first segmented contour volume within the 3D image data; generating a first 2D pattern based on at least a portion of the surface of the first contour or based on at least a portion of the first segmented contour volume; performing a texture analysis on the first 2D pattern; and outputting a texture analysis information.

16 Claims, 1 Drawing Sheet

(51) Int. Cl.

| | |
|---|---|
| *G06T 15/06* | (2011.01) |
| *G06T 7/155* | (2017.01) |
| *G06T 7/11* | (2017.01) |
| *G06T 7/529* | (2017.01) |
| *A61B 6/00* | (2006.01) |
| *A61B 6/03* | (2006.01) |
| *G06T 7/10* | (2017.01) |
| *G06T 11/00* | (2006.01) |

(52) U.S. Cl.
CPC .......... *A61B 6/5223* (2013.01); *G06T 7/0012* (2013.01); *G06T 7/10* (2017.01); *G06T 7/11* (2017.01); *G06T 7/155* (2017.01); *G06T 7/529* (2017.01); *G06T 11/001* (2013.01); *G06T 15/06* (2013.01); *G06T 2200/04* (2013.01); *G06T 2207/10072* (2013.01); *G06T 2207/10081* (2013.01); *G06T 2207/30004* (2013.01); *G06T 2207/30068* (2013.01); *G06T 2207/30096* (2013.01)

(58) Field of Classification Search
CPC ........... G06T 2207/20101; G06T 17/00; G06T 7/149; G06T 7/246; G06T 19/20; G06T 15/04; G06T 2207/10096; G06T 2207/10012; G06T 15/08; G06K 2209/05; G06K 2209/40; G06K 9/20; G06K 9/3241; G06K 2009/4666; G06K 9/00375; G06N 7/005; G06N 20/00
See application file for complete search history.

(56) References Cited

U.S. PATENT DOCUMENTS

| | | |
|---|---|---|
| 9,655,563 B2 | 5/2017 | Liu et al. |
| 2005/0018888 A1* | 1/2005 | Zonneveld .............. A61B 6/00 382/128 |
| 2006/0251307 A1* | 11/2006 | Florin .................... G06T 15/08 382/128 |
| 2006/0274925 A1* | 12/2006 | West ..................... A61N 5/103 382/131 |
| 2011/0090222 A1 | 4/2011 | Ibarz et al. |
| 2012/0026169 A1* | 2/2012 | Bernhardt ............. A61B 6/481 345/424 |
| 2014/0296703 A1* | 10/2014 | Hong .................... A61B 6/463 600/424 |
| 2018/0263706 A1* | 9/2018 | Averbuch ............. A61B 6/5247 |

OTHER PUBLICATIONS

Sahiner, Berkman et al. "Computerized characterization of masses on mammograms: The rubber band straightening transform and texture analysis" Medical Physics, vol. 25, No. 4, pp. 516-526, Apr. 1998 // DOI: 10.1118/1.598228.

Extended European Search Report dated Feb. 22, 2019.

European Office Action dated Feb. 15, 2021 issued in corresponding European Appln. No. 18203636.8.

Liu, H. et al. "Automatic Left Ventricle Segmentation in Cardiac MRI Using Topological Stable-State Thresholding and Region Restricted Dynamic Programming." *Academic Radiology*, vol. 19, No. 6 (2012): pp. 723-731.

* cited by examiner

METHOD AND SYSTEM FOR EVALUATION OF TUMOR TISSUE BY UNFOLDING MORPHOLOGICAL AND TEXTURE PROPERTIES

PRIORITY STATEMENT

The present application hereby claims priority under 35 U.S.C. § 119 to European patent application number EP 17204732.6 filed Nov. 30, 2017, the entire contents of which are hereby incorporated herein by reference.

FIELD

Embodiments of the invention generally relate to a method and system for analyzing an anatomical structure of interest in 3D image data; to a computer program, which performs the steps of an embodiment of the inventive method, if the computer program is executed on an computer; and to an electronically readable storage medium, on which such a computer program is stored.

The method and system of embodiments of the invention are applicable to analyzing any anatomical structure of interest. In particular, they are applicable to analyzing a tumor lesion or tumor tissue.

BACKGROUND

Evaluating tumor tissue in imaging data, e.g. from a diagnostic imaging device (e.g. CT, MR, etc.) is still challenging since the 3-dimensional structure and the individual structural and texture properties of a tumor lesion are hard to evaluate and interpret. Especially detecting tiny properties (small lesions, necrotic areas) or even the distinction between benign and malign tissue is mostly impossible if no other parameters (perfusion or homogeneity parameters, etc.) are available.

Current solutions evaluate tumorous tissue by either evaluating contrast agent dynamics performing either perfusion scans (4D scans, scanning multiple times over the tumor region and looking at the flow characteristics of a tumor tissue) or by scanning with dual- or multiple energy acquisition in computed tomography. While perfusion scans deliver time dependent parameters of the tumor, dual-energy or multi energy solutions result in a static evaluation of the tumor tissue, especially of the iodine distribution in the tumor. Looking at X-ray operated devices, scanning multiple times over the same area result in an increased radiation exposure to the patient and could increase the potential risk for radiation induced cancer. For that reason it is of high relevance to explore alternative methods that either reduces the radiation exposure (when using X-ray devices) or to improve other parameters on non-X-ray devices.

The following methods can directly be used for all types of imaging data and are not bound to X-ray devices only. The following methods are also not only applicable to tumor tissue, but can also be used for other lesion or malformations, especially if the texture features and/or contrast agent dynamics are of interest. In that case, the methods could be used to evaluate bony structures (bone densitometry), hard plaques or soft plaques, or other lesions that might contain differences in a layered structure.

There have been many suggestions in the past the help to gain additional parameters. Following are some concurrent examples:

The method of 4D-Perfusion uses scans at multiple times over the region of interest, but is time consuming and results in high X-ray exposure when operating with X-ray devices.

Performing a dual-energy scan and application of iodine/Tissue decomposition derives the iodine uptake directly without additional scan requirements (Perfusion, Multiple-Phase evaluations). The iodine uptake can deliver suitable parameters for tumor tissue, e.g. malign or benign in breast tissue.

Texture analysis derives texture parameters from the scanned image. The analysis of texture parameters is a useful way of increasing the information obtainable from medical images. It uses radiological images obtained in routine diagnostic practice, but involves an ensemble of mathematical computations performed with the data contained within the images. (Castellano et al., Texture analysis of medical images, Clin Radiol. 2004 December; 59(12): 1061-9). Texture parameters can deliver enhanced information of an anatomical region of interest, e.g. tumor tissue, by inspecting the properties of the tumor. The complexity here lies in the selection of relevant texture parameters. Usually the texture analysis delivers a set of more than >50 parameters that have to be interpreted individually for the lesion of interest. Methods of texture analysis are e.g. described in U.S. Pat. No. 9,655,563 B2.

It can be seen easily that selecting the parameters is a very complex task and can result in very diverse result when multiple radiologists are evaluating the data. One task in texture analysis science is to normalize the texture parameters over all possible acquisition and reconstruction parameters, but this needs a large set of input parameters that can only be solved with deep learning strategies.

A previous approach tried to solve the problem of vast amount of texture feature parameters, by reducing the features to well understood features, like mean, standard deviation, etc.

SUMMARY

At least one embodiment of the present invention provides an improved for performing texture analysis on 3-dimensional structures. At least one embodiment is achieved by the method and at least one embodiment is achieved by a system. Further embodiments of the invention are described in the claims.

One approach is to not only analyse a lesion as a whole, but by creating so called peels/onions. The procedure is done in multiple steps. First, the initial lesion is segmented using a lesion segmentation routine. The result is a 3-dimensional object, and standard parameters from the 3D object can be calculated (WHO criteria, RECIST criteria, diameter, volume, etc.). Afterwards the lesion is processed again using morphological operations. Thereby the initial segmentation is either grown or shrinked in multiple steps, so that the radiologist could have multiple segmentations (like onion peels) of the initial segmentation.

Growing and shrinking the lesion in several steps can cover the coarse segmentation and improve the statistics of the lesion segmentation and following and derived parameters. Nevertheless the onion peels can be either evaluated as shells or full volumes in several stepwise grades, it is still a complex task to evaluate 3-dimensional structures. It is also complicated to do a texture analysis in 3D. The present invention provides an improved method for performing texture analysis on 3-dimensional structures.

According to an embodiment of the invention there is provided a method for analyzing an anatomical structure of interest in 3D image data comprising:
  segmenting a first contour of the structure of interest in the 3D image data, wherein optionally the first contour defines a first segmented contour volume within the 3D image data,
  generating a first 2D pattern based on at least a portion of the surface of the first contour or optionally based on at least a portion of the first segmented contour volume,
  performing a texture analysis on the first 2D pattern, and outputting a texture analysis information.

According to an embodiment of the invention there is provided a system for analyzing an anatomical structure of interest in 3D image data comprising:
  a segmentation unit for segmenting a first contour of the structure of interest in the 3D image data, wherein the first contour defines a first segmented contour volume within the 3D image data,
  a 2D pattern generation unit for generating a first 2D pattern based on at least a portion of the surface of the first contour or based on at least a portion of the first segmented contour volume,
  a texture analysis unit for performing a texture analysis on the first 2D pattern,
  an outputting unit for outputting a texture analysis information.

According to an embodiment of the invention there is provided a system A system for analyzing an anatomical structure of interest in 3D image data, comprising:
  a memory, storing a program including executable instructions; and
  at least one processor to, upon execution of the executable instructions, be configured to
    segment a first contour of the anatomical structure of interest in the 3D image data, wherein the first contour defines a first segmented contour volume within the 3D image data,
    generate a first 2D pattern based on at least a portion of the surface of the first contour or based on at least a portion of the first segmented contour volume,
    perform a texture analysis on the first 2D pattern, and
    control outputting of texture analysis information, obtained based upon the texture analysis performed, for analyzing the anatomical structure of interest in the 3D image data.

An embodiment of the invention also relates to a medical imaging system, such as a computed tomography system, which includes a central processing unit or a computer for the evaluation of image data, wherein the method according to an embodiment of the invention is implemented on the central processing unit or the computer of the medical imaging system.

According to another embodiment of the present invention, it is provided that components of the system are part of a network, wherein preferably the network and a medical imaging system which provides the 3D image data are in communication with each other. Such a networked solution could be implemented via an internet platform and/or in a cloud-based computing system.

An embodiment of the invention further provides a computer-readable medium on which are stored a program elements that can be read and executed by a computer unit in order to perform steps of the method according to an embodiment of the invention and its various embodiments when the program elements are executed by the computer unit.

An embodiment of the invention further provides a computer program product with program elements that can be read and executed by a computer unit in order to perform steps of the method according to any embodiment of the invention and its various embodiments when the program elements are executed by the computer unit.

Thus, there is provided a computer program, which performs the steps of a method according to an embodiment of the method if the computer program is executed on an computer.

An embodiment of the invention further provides a memory, storing a computer program which, upon the computer program being executed on a computer, performs an embodiment of the method.

An embodiment of the invention further provides a non-transitory electronically readable storage medium, storing a computer program which, upon the computer program being executed on a computer, performs an embodiment of the method.

Further there is provided an electronically readable storage medium, on which a computer program according to an embodiment is stored.

BRIEF DESCRIPTION OF THE DRAWINGS

Further details and advantages of the current invention can be taken from the following description of example embodiments in conjunction with the drawings.

The method is of an embodiment of the invention is shown and illustrated schematically in in the Figures, which show.

DETAILED DESCRIPTION OF THE EXAMPLE EMBODIMENTS

Figure 1:
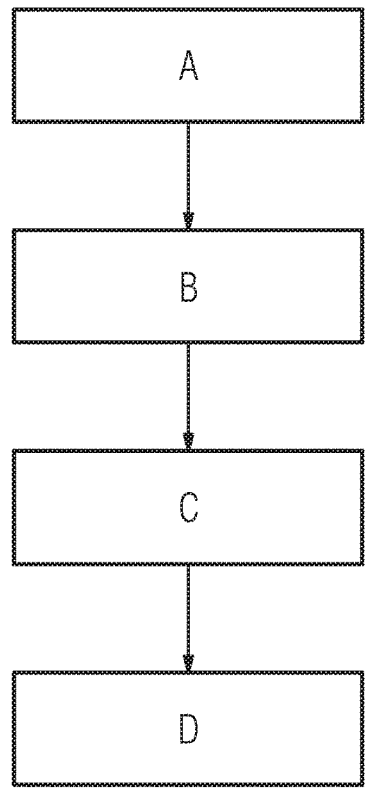
FIG. 1: a schematic representation of the method of an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to an embodiment of the invention there is provided a method for analyzing an anatomical structure of interest in 3D image data comprising:
  segmenting a first contour of the structure of interest in the 3D image data, wherein optionally the first contour defines a first segmented contour volume within the 3D image data,
  generating a first 2D pattern based on at least a portion of the surface of the first contour or optionally based on at least a portion of the first segmented contour volume,
  performing a texture analysis on the first 2D pattern, and
  outputting a texture analysis information.

An anatomical structure may be any structure to be analyzed in at least a portion of a patient's anatomy. A non-limiting list of examples includes a bone structure, a bone, an organ, a blood vessel, a tumor, a plaque (as found e.g. in a blood vessel), a tissue, a cyst, a foreign object inside a patient's body, or combinations, portions, or sub-structures of the above mentioned examples. In particular, an anatomical structure may also be referred to as a "lesion", as in, for example, a tumor lesion or a plaque lesion.

The 3D image data may be provided by any suitable method or imaging device including, but not limited to computed tomography (CT), magnetic resonance tomography (MR), positron emission tomography, tomosynthesis, ultrasound, and combinations of such methods or imaging devices Segmenting a contour of a structure in 3D image date is achieved by image segmentation. Image segmentation the process of partitioning a digital image into multiple segments to locate objects and boundaries (lines, curves, etc.) in images and generally comprises the process of assigning a label to every pixels or voxels in an image such that pixels or voxels with the same label share certain characteristics. This results in a set of segments or a set of contours extracted from the image. A non-limiting list of examples includes image segmentation methods includes edge detection, histogram based segmentation, watershed transformation, graph cuts segmentations, random walker segmentation, segmentation using artificial intelligence, such as trained segmentation, neural networks, or machine learning.

The step of segmenting provides a contour of the structure which. In the case of 3D image data can be thought of as a curved surface. In some cases, e.g. when an anatomical structure has a defined volume which is included in the 3D image data, the curved surface of the contour may enclose a finite volume. In this case, the the first contour defines a first segmented contour volume within the 3D image data. In case the anatomical structure is for example a tumor lesion, the contour may represent the outer surface or delimitation of the tumor lesion and entirely encloses the tumor lesion volume.

The step of generating a first 2D pattern based on at least a portion of the surface of the first contour or optionally based on at least a portion of the first segmented contour volume generally comprises a step of unfolding at least a portion of the curved surface of the contour onto a 2D plane. Further it may include projecting image information contained in the curved surface or in at least a portion of a volume enclosed or otherwise delimited by the curved surface onto the 2D plane.

The generated 2D pattern may itself have a 2D contour which can be e.g. a curved line. The generated 2D pattern contains image information and is then subjected to a texture analysis. The texture of an image comprises information about the spatial distribution of image parameters such as color or intensity and can be described and analyzed by such parameters as for example and without limitation contrast, intensity, entropy, fineness, coarseness, smoothness, granularity, periodicity, patchiness. In particular, texture analysis allows differentiation of image textures not readily visible to the human eye and is useful for example for differentiation between healthy and diseased tissue. Texture analysis can be performed by various computational methods including artificial intelligence based methods, such as machine learning, deep learning and use of neural networks. Texture features can be input for machine learning a classifier and for using a machine learnt classifier. Rather than or in addition to using formula-based texture features, data driven texture features can be derived from training images. The texture analysis provides a texture analysis information with regard to the anatomical structure, which may be a qualitative or quantitative information including for example a probability information, a classification into a plurality of classes. Non-limiting examples include healthy/diseased, normal/abnormal, tumor classes, plaque classes, etc.

The texture analysis information is then outputted, e.g. to a data interface, to a user, e.g. via a display device, to a data storage device or into a data network.

According to an embodiment of the invention, the method additionally comprises the step of outputting the 2D pattern to a data interface, a data storage device or a data display device.

According to an embodiment of the invention, the method further comprises the step of generating at least one further contour based on the first contour of the structure wherein optionally the at least one further contour defines at least a further segmented contour volume within the 3D image data. According to this embodiment, the first contour and the further contour may be used to define a first contour volume, a second contour volume, and a segmented peel volume which is delimited by the first contour and the at least one further contour.

According to an embodiment of the invention, the first contour is enclosed by the at least one further contour. According to an alternative embodiment of the invention, the at least one further contour is enclosed by the first contour. Thus, the first and at least one further contour define a segmented peel volume which is delimited by the first contour and the at least one further contour.

According to an embodiment of the invention, the at least one further contour is generated by expanding or shrinking the first contour. This may be e.g. achieved by an algorithmic operation of expanding or shrinking the volume which is (either fully or partially) enclosed by the contour. According to this embodiment, the first contour and the further contour may be used to define a first contour volume, a second contour volume, and a segmented peel volume which is delimited by the first contour and the at least one further contour.

According to an embodiment of the invention, the at least one further contour has substantially the same shape as the first contour. According to this embodiment, the first contour and the further contour may be used to define a first contour volume, a second contour volume, and a segmented peel volume which is delimited by the first contour and the at least one further contour.

According to an embodiment of the invention, a plurality of further contours are generated, thereby creating a plurality of further segmented contour volumes. According to this embodiment, the first contour and the plurality of n further contours may be used to define n+1 segmented contour volumes, namely the first contour volume defined by the first contour and n contour volumes defined by the n further contours.

According to an embodiment of the invention, at least one segmented peel volume is defined by two different contours. This segmented peel volumes may be viewed in analogy to a peel of an onion which is defined by an outer and inner surface and surrounds an inner volume of the onion.

Further according to this embodiment, the first contour and the plurality of n further contours may be used to define n segmented peel volumes each of which are delimited by two adjacent contours. These segmented peel volumes may be viewed in analogy to a successive peels of an onion. Additional segmented peel volumes may be defined by non-adjacent contours.

According to an embodiment of the invention, a plurality of 2D patterns are generated based on at least a portion of the surface of a plurality of contours or based on at least a portion of a plurality of segmented contour volumes or based on at least a portion of a plurality of segmented peel volumes and wherein the step of texture analysis is being carried out on each of the unfolded 2D patterns.

According to an embodiment of the invention, a plurality of 2D patterns having a different size are normalized to a normalized size.

According to an embodiment of the invention, the method additionally comprises the step of outputting the plurality of 2D patterns to a data interface, a data storage device or a data display device. Thus in addition to performing the texture analysis, a user can visually inspect a series of 2D patterns "peel by peel". This may be useful for locating e.g. a sub-structure within the structure. Another use scenario would be to e.g. visualize or analyze myocardial perfusion information "peel by peel", i.e. in successive layers of the heart muscle.

According to an embodiment of the invention, the step of generating a 2D pattern comprises ray-casting from an interior central part of a segmented contour volume.

According to an embodiment of the invention there is provided a system for analyzing an anatomical structure of interest in 3D image data comprising:
  a segmentation unit for segmenting a first contour of the structure of interest in the 3D image data, wherein the first contour defines a first segmented contour volume within the 3D image data,
  a 2D pattern generation unit for generating a first 2D pattern based on at least a portion of the surface of the first contour or based on at least a portion of the first segmented contour volume,
  a texture analysis unit for performing a texture analysis on the first 2D pattern,
  an outputting unit for outputting a texture analysis information.

The system according to an embodiment of the present invention or specific components of the system, may be provided in a medical imaging system such as a CT scanner.

An embodiment of the invention also relates to a medical imaging system, such as a computed tomography system, which includes a central processing unit or a computer for the evaluation of image data, wherein the method according to an embodiment of the invention is implemented on the central processing unit or the computer of the medical imaging system.

According to another embodiment of the present invention, it is provided that components of the system are part of a network, wherein preferably the network and a medical imaging system which provides the 3D image data are in communication with each other. Such a networked solution could be implemented via an internet platform and/or in a cloud-based computing system.

An embodiment of the invention further provides a computer-readable medium on which are stored a program elements that can be read and executed by a computer unit in order to perform steps of the method according to an embodiment of the invention and its various embodiments when the program elements are executed by the computer unit.

An embodiment of the invention further provides a computer program product with program elements that can be read and executed by a computer unit in order to perform steps of the method according to any embodiment of the invention and its various embodiments when the program elements are executed by the computer unit.

Thus, there is provided a computer program, which performs the steps of a method according to an embodiment of the method if the computer program is executed on an computer.

Further there is provided an electronically readable storage medium, on which a computer program according to an embodiment is stored.

Before discussing example embodiments in more detail, it is noted that some example embodiments may be described with reference to acts and symbolic representations of operations (e.g., in the form of a flow diagram, structure diagrams, block diagram, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure.

FIG. 1 shows a schematic representation of the method of an embodiment of the invention. In step A, a first contour of the structure of interest is segmented in the 3D image data, wherein optionally the first contour defines a first segmented contour volume within the 3D image data.

In step B a first 2D pattern is generated based on at least a portion of the surface of the first contour or optionally based on at least a portion of the first segmented contour volume.

In step C a texture analysis on the first 2D pattern.

In step D a texture analysis information is outputted.

An embodiment of the present invention solves the complexity of 3D dimensional structures by unfolding the structure into 2-dimensional patterns. Preferably, this is done by either using multiple segmented peel volumes (the "onion peels") or multiple 3D volumes that have been created by generating at least one first contour of the anatomical structure, e.g. a lesion, and one or more further contours e.g. by using the "peel method", i.e. by expanding or shrinking the first contour to create further contours.

One example of the underlying method of an embodiment of the invention for generating a 2D pattern is to perform a ray-casting from the interior central part of the segmented lesion, going from the central part of the lesion and integrating all voxels that hit the ray on its way through the volume. It is of high relevance to understand that this method operates in 3D and it is used to reduce the complex 3-dimensional interpretation to a 2-dimensional representation.

The suggested method can either be performed on individual peel volumes that only contain the peel content without the inner core volume data (FIG. 2) or on full volumes defined by different contours.

Figure 2:
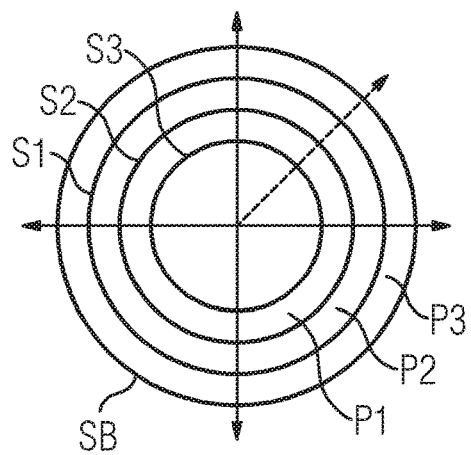
FIG. 2: a schematic representation of certain embodiments of the invention.

In FIG. 2 the first contour, i.e. the segment boundary (SB), of an anatomical structure such as a tumor lesion is schematically depicted. Although the schematic depiction in FIG. 2 is shown in 2D, in reality the tumor lesion is three-dimensional. The segmented first contour SB in this schematic representation can thus be thought of a spherical closed surface. Further contours, i.e. boundaries S1, S2, and S3, are generated by shrinking the first contour (segment boundary SB). Alternatively, further contours could also be generated by expanding the segmented first contour. In both alternatives (shrinking or expanding) the result is a set of successive contours separated by segmented peel volumes ("peels" P1, P2, P3), analogous to an onion with successive peels. In FIG. 2 each segmented peel volume P1, P2, P3 is shown as indicated. For example, peel P2 and peel P3 contain a lesion, whereas Peel 1 does not contain a lesion. Although FIG. 2 is a simplified drawing to show the situation in 2D, but the real problem lies in the analysis of 3D image data.

Using the unfold method the 3-dimensional surface of each peel can be drawn in 2D and a quick overview of the individual peels can be visualized. Each peel, of course has a different surface size, but also here using the unfolding method the difference in area size can be normalized by simply projecting the surface of the peel to the largest surface size.

The method also scales with the thickness of the peel border because the method integrates along the path of the ray-casting method. Although the suggestion here is to use an integration method, other methods could use maximum or minimum intensity projections (MIP, MinIP) or other nonlinear methods to obtain the 2D pattern.

Another suggestion is to not only use peels, but also use full volumes defined by each of the contours, where the effect of MIP or MinIP might be more obvious.

Having a 2-dimensional projection of lesions is also helpful to reduce the 3-dimensional problems in texture analysis. Thereby the reduction to a 2-dimensional problem could improve performance and also help improving the normalization of texture features.

In the above example, the method has been described for a contour fully enclosing an anatomical structure of interest. In some cases it may not be possible or desirable to generate a contour fully enclosing the anatomical structure of interest. This may be due to the nature of the anatomical structure of interest or because the image data only partially represents an anatomical structure. For example, in case the anatomical structure is an open ended vessel structure, and the anatomical structure of interest is only a portion of the entire anatomical structure. In this case the method of the invention may be applied to the portion of the entire anatomical structure. The step of segmenting may result in an open ended contour. In this case, the method of the invention is applied to the open ended contour. Alternatively, a closed contour may be generated by arbitrarily defining a closure of the contour. In the example where the anatomical structure is a vessel structure, a user may choose to arbitrarily analyze only a defined portion of the vessel structure and the first contour may be a roughly cylindrical contour with an arbitrarily defined length which represents a corresponding vessel segment. In case ray casting is used to generate a 2D pattern of such a cylinder-like shape (or a sphere-like shape), the ray-casting may be performed by casting rays along a center line of the cylinder-like shape (or, respectively, from the center of a sphere-like shape).

Figure 3:
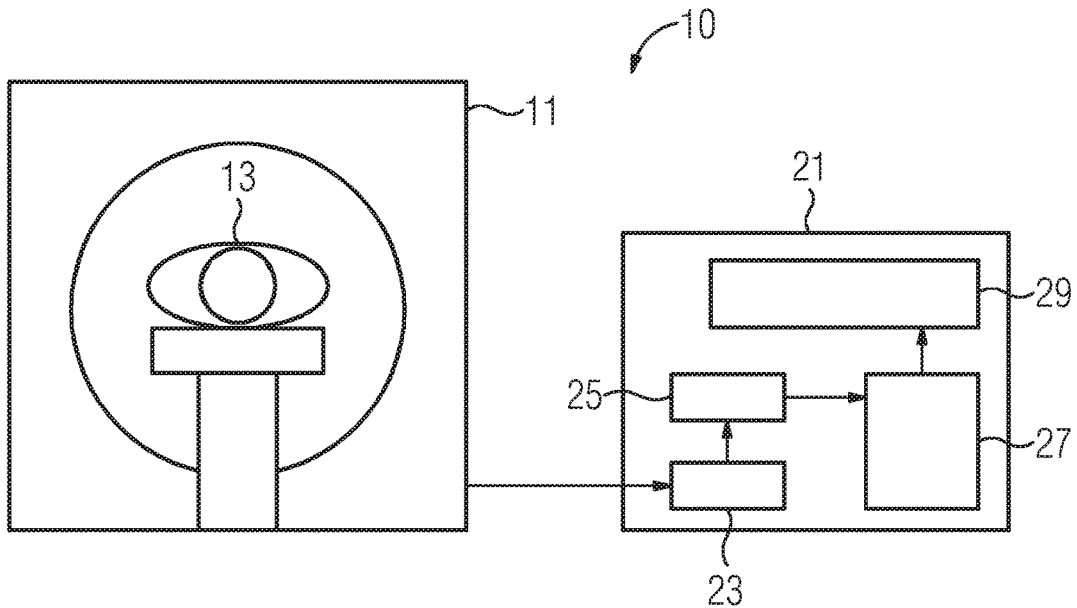
FIG. 3: a schematic representation of a medical imaging system according to an embodiment of the invention.

FIG. 3 schematically shows a medical imaging system 10 which in this example embodiment comprises a CT scanner 11 suitable for scanning an anatomy of interest of a patient 13. The CT scanner 11 is connected to a system 21 for analyzing the anatomical structure of interest in 3D image data. The system 21 may be comprised in the control system of the medical imaging system.

The system 21 comprises a segmentation unit 23 for segmenting a first contour of the structure of interest in the 3D image data, wherein the first contour defines a first segmented contour volume within the 3D image data.

The system 21 further comprises a 2D pattern generation unit 25 for generating a first 2D pattern based on at least a portion of the surface of the first contour or based on at least a portion of the first segmented contour volume.

The system 21 further comprises a texture analysis unit 27 for performing a texture analysis on the first 2D pattern, The system 21 further comprises an outputting unit 29 for outputting a texture analysis information. Outputting the texture analysis information may comprise any device(s) of outputting information generally known, such to a data interface, a data storage device or a data display device.

The system according to an embodiment of the present invention or specific components of the system, may be provided in a medical imaging system such as a CT scanner, MRI scanner or similar.

Some or all components, units and/or devices of the system may be implemented using hardware, software, and/or a combination thereof. For example, hardware devices may be implemented using processing circuitry such as, but not limited to, a processor, a microcomputer, a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory.

Although the present invention has been described in detail with reference to the example embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for analyzing an anatomical structure of interest in 3D image data, comprising:
segmenting a first contour of the anatomical structure of interest in the 3D image data, wherein the first contour defines a first segmented contour volume within the 3D image data;
generating a first 2D pattern by unfolding at least a portion of a surface of the first contour or by unfolding at least a portion of the first segmented contour volume;
performing a texture analysis on the first 2D pattern;
generating a plurality of further contours based on the first contour of the anatomical structure, wherein the plurality of further contours define a plurality of further segmented contour volumes within the 3D image data, and wherein a plurality of segmented peel volumes are each defined by two different contours among the first contour and the plurality of further contours; and
outputting texture analysis information for analyzing the anatomical structure of interest in the 3D image data, the texture analysis information being based on the texture analysis.

2. The method of claim 1, wherein the first contour is enclosed by at least one further contour of the plurality of further contours, or wherein the at least one further contour is enclosed by the first contour.

3. The method of claim 1, wherein the generating the plurality of further contours includes generating at least one further contour by expanding or shrinking the first contour.

4. The method of claim 1, wherein the plurality of further contours have a substantially same shape as the first contour.

5. The method of claim 1, further comprising:
generating a plurality of 2D patterns based on at least a portion of the surface of the plurality of further contours or based on at least a portion of a plurality of segmented contour volumes,
wherein the performing the texture analysis is performed on each of the plurality of 2D patterns.

6. The method of claim 5, further comprising:
normalizing 2D patterns having a different size, of the plurality of 2D patterns, to a normalized size.

7. The method of claim 1, wherein the generating the first 2D pattern comprises ray-casting from an interior central part of the first segmented contour volume.

8. The method of claim 1, wherein the outputting includes outputting to a data interface, a data storage device, or a data display device.

9. A system for analyzing an anatomical structure of interest in 3D image data, comprising:
processing circuitry configured to cause the system to,
segment a first contour of the anatomical structure of interest in the 3D image data, wherein the first contour defines a first segmented contour volume within the 3D image data,
generate a first 2D pattern by unfolding at least a portion of a surface of the first contour or by unfolding at least a portion of the first segmented contour volume,
perform a texture analysis on the first 2D pattern,
generate a plurality of further contours based on the first contour of the anatomical structure, wherein the plurality of further contours define a plurality of further segmented contour volumes within the 3D image data, and wherein plurality of segmented peel volumes are each defined by two difference contours among the first contour and the plurality of further contours, and
control outputting of texture analysis information for analyzing the anatomical structure of interest in the 3D image data, the texture analysis information being based on the texture analysis.

10. A non-transitory electronically readable storage medium, storing a computer program which, when executed by processing circuitry, causes a computer to:
   segment a first contour of an anatomical structure of interest in 3D image data, wherein the first contour defines a first segmented contour volume within the 3D image data;
   generate a first 2D pattern by unfolding at least a portion of a surface of the first contour or by unfolding at least a portion of the first segmented contour volume;
   perform a texture analysis on the first 2D pattern;
   generate a plurality of further contours based on the first contour of the anatomical structure, wherein the plurality of further contours define a plurality of further segmented contour volumes within the 3D image data, and wherein a plurality of segmented peel volumes are each defined by two different contours among the first contour and the plurality of further contours; and
   output texture analysis information for analyzing the anatomical structure of interest in the 3D image data, the texture analysis information being based on the texture analysis.

11. The method of claim 2, wherein the at least one further contour is generated by expanding or shrinking the first contour.

12. The method of claim 2, wherein the at least one further contour has a substantially same shape as the first contour.

13. The method of claim 1, further comprising
   generating a plurality of 2D patterns based on one of at least a portion of the surface of a plurality of contours, at least a portion of a plurality of segmented contour volumes, or at least a portion of the plurality of segmented peel volumes,
   wherein the performing the texture analysis is performed on each of the plurality of 2D patterns.

14. A system for analyzing an anatomical structure of interest in 3D image data, comprising:
   a memory, storing a program including executable instructions; and
   at least one processor configured to, upon execution of the executable instructions, be configured to,
      segment a first contour of the anatomical structure of interest in the 3D image data, wherein the first contour defines a first segmented contour volume within the 3D image data,
      generate a first 2D pattern by unfolding at least a portion of a surface of the first contour or by unfolding at least a portion of the first segmented contour volume,
      perform a texture analysis on the first 2D pattern,
      generate a plurality of further contours based on the first contour of the anatomical structure, wherein the plurality of further contours define a plurality of further segmented contour volumes within the 3D image data, and wherein a plurality of segmented peel volumes are each defined by two different contours among the first contour and the plurality of further contours, and
      control outputting of texture analysis information for analyzing the anatomical structure of interest in the 3D image data, the texture analysis information being based on the texture analysis.

15. The system of claim 9, further comprising:
a computed tomography scanner.

16. The system of claim 14, further comprising:
a computed tomography scanner.

* * * * *